United States Patent [19]

Enomoto et al.

[11] Patent Number: 4,594,345

[45] Date of Patent: Jun. 10, 1986

[54] METHYLFLAVONE-8-CARBOXYLATES

[75] Inventors: Hiroshi Enomoto, Nagaokakyo; Tadatoshi Nomura, Uji; Yoshiaki Aoyagi, Otsu; Shoichi Chokai, Kameoka; Masao Murase, Kusatsu; Kichiro Inoue; Ichiro Shirahase, both of Kyoto, all of Japan

[73] Assignee: Nippon Shinyaku Co. Ltd., Japan

[21] Appl. No.: 507,692

[22] Filed: Jun. 24, 1983

[30] Foreign Application Priority Data

Jun. 23, 1982 [JP] Japan ................. 57-108928

[51] Int. Cl.[4] ............. A61K 31/35; C07D 311/30

[52] U.S. Cl. ................... 514/234; 514/456; 514/320; 514/420; 549/403; 548/525; 546/196; 544/151

[58] Field of Search ............ 549/403; 424/283; 548/525; 546/196; 544/151; 514/456, 320, 422, 234

[56] References Cited

U.S. PATENT DOCUMENTS 3,350,411 10/1967 Da Re ................... 549/403
3,770,802 11/1973 Sianesi ................... 549/403

*Primary Examiner*—Nicky Chan
*Attorney, Agent, or Firm*—Jacobs & Jacobs

[57] ABSTRACT 3-methylflavone derivatives which are useful in the treatment of allergies, asthma and inflammation.

11 Claims, No Drawings

METHYLFLAVONE-8-CARBOXYLATES

The present invention relates to 3-methylflavone derivatives and their use in the treatment of allergic diseases, asthma, and inflammation.

In particular, the present invention relates to a compound of the formula (I):

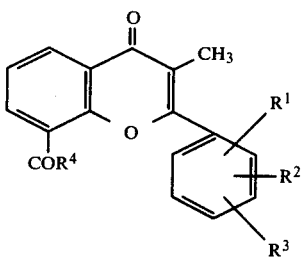

wherein $R^1$, $R^2$ and $R^3$ are the same or different and are hydrogen, halogen, alkyl of 1 to 15 carbon atoms in total and 1 to 10 carbon atoms in the longest chain, preferably lower alkyl, or lower alkoxy, $R^4$ is hydroxy, lower alkoxy, (hydroxy)lower alkoxy or

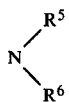

wherein $R^5$ is hydrogen or lower alkyl and $R^6$ is lower alkyl or cycloalkyl of 5 to 7 carbon atoms, or $R^5$ and $R^6$ together with the nitrogen atom to which they are attached form a five to seven membered heterocyclic ring which may contain N, O or S as an additional hetero atom; and when $R^4$ is hydroxy, pharmaceutically acceptable salts thereof.

The compounds (I) of the present invention have marked antiallergic, anti-inflammatory and expectorant activity, and are useful in the treatment of allergic diseases, inflammation and asthma. These compounds (I) may be administered orally and have long lasting activity, in contrast with prior art compounds.

For example, sodium cromoglicate recently developed is reported by Cox, et al. that it is effective for allergic asthma (cf. Advances in Drug Research, volume 5, page 115, 1970). It is believed that this compound inhibits emission of chemical mediators from mast cells. Unfortunately, this compound does not show any pharmaceutical effect by oral administration and further its action is of short duration.

Recently, it has been known that SRS-A (slow reacting substance of anaphylaxia) is one of the chemical mediators that play a main role at the onset of asthma. Development of antagonizing agents against the action of SRS-A is thus desirable. The compounds (I) of the present invention exhibit a strong SRS-A antagonizing and synthesis inhibiting action.

As used herein, alkyl, lower alkyl and lower alkoxy include straight or branched hydrocarbon chains. Lower alkyl and lower alkoxy mean alkyl and alkoxy, respectively, of 1 to 6 carbon atoms, preferably with 1 to 4 and most preferably 1 to 3 carbon atoms. It is also preferred that lower alkyl and lower alkoxy have 1 to 4, most preferably 1 to 3, carbon atoms in the longest hydrocarbon chain.

Examples of alkyl include methyl, ethyl, propyl, isopropyl, butyl, isobutyl, tertiary butyl, pentyl, hexyl, heptyl, octyl and the like. Examples of halogen include fluorine, chlorine, bromine, iodine and the like, preferably chlorine and bromine. Examples of lower alkoxy include methoxy, ethoxy, propoxy, isopropoxy, butoxy, tertiary butoxy and the like. Examples of (hydroxy)-lower alkoxy include hydroxymethoxy, β-hydroxyethoxy, gamma-hydroxypropoxy and the like.

Examples of

include methylamino, ethylamino, propylamino, isopropylamino, butylamino, tertiary butylamino, pentylamino, hexylamino, cyclopentylamino, cyclohexylamino, cycloheptylamino, dimethylamino, ethyl methylamino, diethylamino, methyl propylamino, ethyl propylamino, dipropylamino, butyl methylamino, butyl ethylamino, dibutylamino and the like. Examples where $R^5$ and $R^6$ are bonded to form a ring include pyrrolidino, piperidino, morpholino and the like.

Representative examples of the compounds of the present invention are as follows:

Methyl 3-methylflavone-8-carboxylate, 3-methylflavone-8-carboxylic acid N,N-diethylamide, 2'-methoxy-3-methylflavone-8-carbroxylic acid, 2'-methoxy-3-methylflavone-8-methylflavone-8-carboxylic acid, ethyl 2'-methoxy-3-methylflavone-8-carboxylate, 2'-methoxy-3-methylflavonve-8-carboxylic acid N,N-diethylamide, 2'-methoxy-3-methylflavone-8-carboxylic acid N,N-diethylamide, 2'-methoxy-3-methylflavone-8-carboxylic acid acid N-ethylamide, 3'-methoxy-3-methylflavone-8-carboxylic acid, 4'-methoxy-3-methylflavone-8-carboxylic acid, ethyl 4'-methoxy-3-methylflavone-8-carboxylate, 4'-methoxy-3-methylflavone-8-carboxylic acid N,N-diethylamide, 4'-methoxy-3-methylflavoen-8-carboxylic acid N-ethylamide, 2'-ethoxy-3-methylflavone-8-carboxylic acid, ethyl 2'-ethoxy-3-methylflavone-8-carboxylate, beta-hydroxyethyl 2'-ethoxy-3-methylflavone-8-carboxylate, 2'-ethoxy-3-methylflavone-8-carboxylic acid N,N-diethylamide, 2'-ethoxy-3-methylflavone-8-carboxylic acid N-ethylamide, 2'-isopropoxy-3-methylflavone-8-carboxylic acid, ethyl 2'-isopropoxy-3-methylflavone-8-carboxylate, 2'-isopropoxy-3-methylflavone-8-carboxylic acid N,N-diethylamide, 2',3'-dimethoxy-3-methylflavone-8-carboxylic acid, ethyl 2'.3'-dimethoxy-3-methylflavone-8-carboxylate, 3',4'-dimethoxy-3-methylflavone-8-carboxylic acid, 2',4'-dimethoxy-3-methylflavone-8-carboxylic acid, ethyl 2',4'-dimethoxy-3-methylflavone-8-carboxylate, 2',4'-dimethoxy-3-methylflavone-8-carboxylic acid N,N-diethylamide, 2',3',4'-trimethoxy-3-methylflavone-8-carboxylic acid, ethyl 2',3',4'-trimethoxy-3-methylflaveone-8-carboxylate, 2',3',4'-trimethoxy-3-methylflavone-8-carboxylic acid N,N-diethylamide, 3',4',5'-trimethoxy-3-methylflavone-8-carboxylic acid, 2',3-dimethylflavone-8-carboxylic acid, 2',3-dimethylflavone-8-carboxylic acid ethyl ester, 2',3-dimethylflavone-8-carboxylic acid N,N-diethylamide, 2'-ethyl-3-methylflavone-8-carboxylic acid, ethyl 2'-ethyl-3-methylflavone-8-carboxylate, 2'-ethyl-3-methylflavone-8-carboxylic acid N,N-diethylamide, 2',3,4'-trimethylflavone-8-carboxylic acid, ethyl 2',3,4'- trimethylflavone-8-carboxylate, beta-hydroxyethyl 2'.3.4'-trimethylflavone-8-carboxylate, 2',3,4'-trimethylflavone-8-carboxylic acid N,N-diethylamide, 2',3,4'-trimethylflavone-8-carboxylic acid N-n-butyl-N-ethylamide, 4'-ethyl-3-methylflavone-8-carboxylic acid, ethyl 4'-ethyl-3-methylflavone-8-carboxylate, 4'-ethyl-3-methylflaveone-8-carboxylic acid N,N-diethylamide, 4'-isopropyl-3-methylflavone-8-carboxylic acid, ethyl 4'-isopropyl-3-methylflavone-8-carboxylate, 4'-isopropyl-3-methylflavone-8-carboxylic acid N-ethylamide, 4'-isopropyl-3-methylflavone-8-carboxylic acid N-n-hexylamide, 4'-isopropyl-3-methylflavone-8-carboxylic acid N-cyclohexylamide, 4'-isopropyl-3-methylflavone-8-carboxylic acid N,N-diethylamide, 4'-isopropyl-3-methylflavone-8-carboxylic acid N-n-butyl-N-ethylamide, 4'-isopropyl-3-methylflavone-8-carboxylic acid N,N-di-n-butylamide, 4'-isopropyl-3-methylflavone-8-carboxylic acid N,N-pentamethylene amide, 4'-tertiary butyl-3-methylflavone-8-carboxylic acid, ethyl 4'-tertiary butyl-3-methylflavone-8-carboxylate, 4'-tertiary butyl-3-methylflavone-8-carboxylic acid N,N-diethylamide, 3-methyl-4'-n-pentylflavone-8-carboxylic acid, ethyl 3-methyl-4'-n-pentylflavone-8-carboxylate, 3-methyl-4'-n-pentylflavone-8-carboxylic acid N,N-diethylamide, 3-methyl-4'-n-octylflavone-8-carboxylic acid, ethyl 3-methyl-4'-n-octylflavone-8-carboxylate, 3-methyl-4'-n-octylflavone-8-carboxylic acid N,N-diethylamide, 3-methyl-4'-n-octylflavone-8-carboxylic acid N-ethylamide, 2'-chloro-3-methylflavone-8-carboxylic acid, ethyl 2'-chloro-3-methylflavone-8-carboxylate, beta-hydroxyethyl 2'-chloro-3-methylflavone-8-carboxylate, 4'-chloro-3-methylflavone-8-carboxylic acid, ethyl 4'-chloro-3-methylflavone-8-carboxylate, beta-hydroxyethyl 4'-chloro-3-methylflavone-8-carboxylate, 4'-chloro-3-methylflavone-8-carboxylic acid N,N-diethylamide, 4'-chloro-3-methylflavone-8-carboxylic acid N-ethylamide, 2',4'-dichloro-3-methylflavone-8-carboxylic acid, ethyl 2',4'-dichloro-3-methylflavone-8-carboxylate, 2',4'-dichloro-3-methylflavone-8-carboxylic acid N,N-diethylamide, 2',5'-dichloro-3-methylflavone-8-carboxylic acid, ethyl 2',5'-dichloro-3-methylflavone-8-carboxylate, 2',5'-dichloro-3-methylflavone-8-carboxylic acid N,N-diethylamide.

The compounds (I) according to the present invention can be produced by various routes as shown below.

Method 1

U.S. Pat. No. 2,921,070, Japan Examined Patent Publication No. Sho-41-7953.

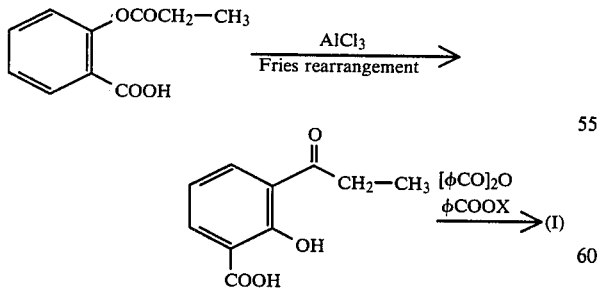

φ means phenyl substituted with R¹, R² and R³
X means alkali metal

Thus, 2-propionyloxybenzoic acid is heated with anhydrous aluminum chloride in a Fries rearrangement and the resulting 3-carboxy-2-hydroxypropiophenone is heated with benzoic anhydride and alkali benzoate at 180° to 190° C. to afford 3-methylflavone-8-carboxylic acid derivatives.

Method 2

Japan Unexamined Patent Publication No. Sho-49-80035.

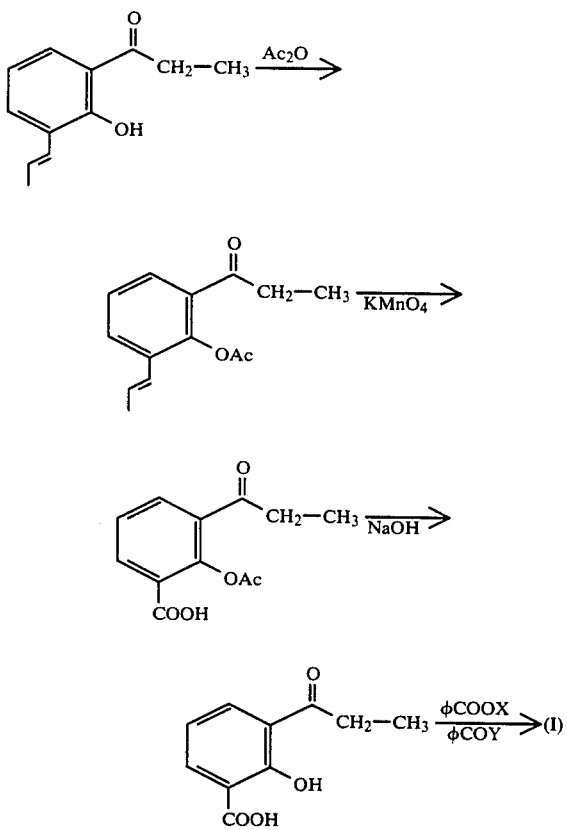

φ and X are the same as already defined
Y is halogen; Ac is acetyl

Thus, 2-hydroxy-3-propenylpropiophenone is acetylated, oxidized with a suitable oxidizing agent such as potassium permanganate, the resulting carboxylic acid is deacetylated, and heated with benzoic halide and alkali benzoate at 185° to 195° C. to give 3-methylflavone-8-carboxylic acid derivatives.

Method 3

Japan examined Patent Publication No. Sho-51-6150.

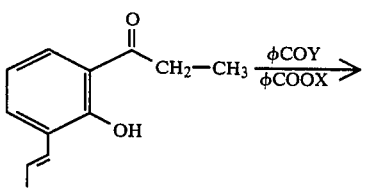

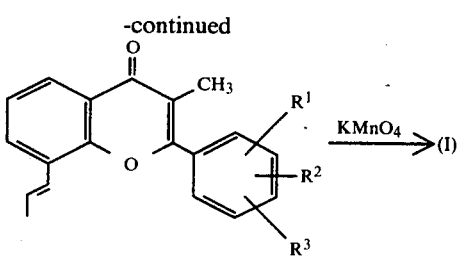

Thus, 2-hydroxy-3-propenylpropiophenone is heated with benzoic halide and alkali benzoate at 180° to 190° C. and the resulting 3-methyl-8-propenylflavone derivative is oxidized with an oxidizing agent such as potassium permanganate to afford 3-methylflavone-8-carboxylic acid derivatives.

In the methods 1 to 3, sodium benzoate is used as a base in the ring closure reaction to form methylflavone. When the above ring closure method is applied in synthesizing 3-methylflavone derivatives having various substituent(s) at 2-phenyl, some benzoic acid derivatives with substituent(s) are very expensive and the yield of the products may be very poor depending upon the substituent(s) applied. Further, the recovery rate of benzoic acid after the reaction is comparatively poor.

In order to avoid such disadvantages, the following methods have been devised according to the present invention.

Method 4

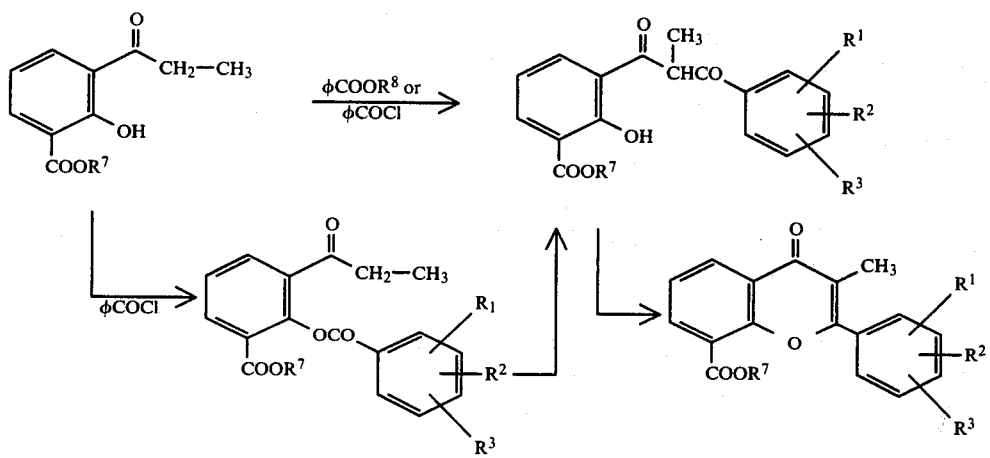

In the formulas, $\phi$, $R^1$, $R^2$ and $R^3$ are the same as already defined and $R^7$ and $R^8$ are lower alkyl.

Method 5

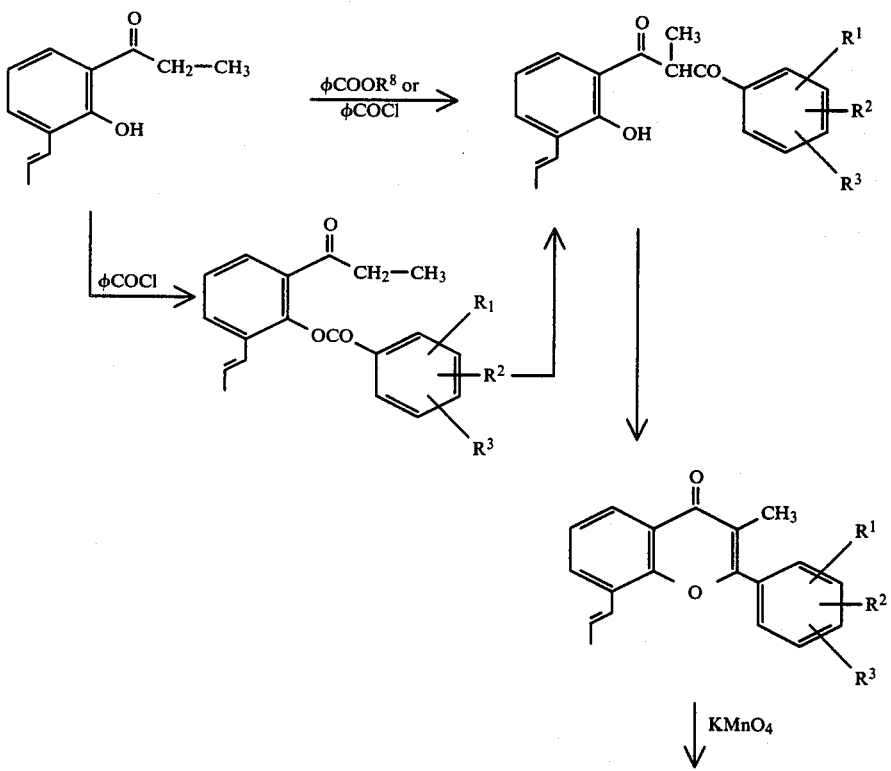

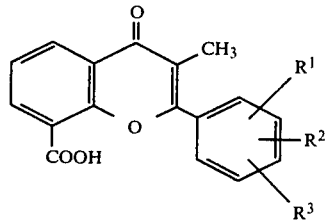

(II)

In the formulas, φ, R$^1$, R$^2$, R$^3$ and R$^8$ are the same as already defined.

With reference to methods 4 and 5, detailed illustrations are as follows.

Method 4

3-Propionylsalicylate is made to react with substituted benzoic acid chloride or with substituted benzoate at 50° to 100° for two to eight hours in the presence of two or more equivalents (preferably, 2.1 to 6 equivalents) of base (such as, for example, sodium hydride, sodium alkoxides, and the like) in a suitable solvent (such as, for example, dimethyl formamide, tetrahydrofuran, dioxan and the like) to afford 3-(alpha-substituted benzoylpropionyl)-salicylate.

This compound may also be prepared by the following way. Thus, 3-propionylsalicylate is made to react with substituted benzoic acid chloride at −10° C. to room temperature for one to twenty four hours in the presence of suitable amount of base (such as, for example, sodium hydride, sodium alkoxides, potassium carbonate, pyridine, triethylamine and the like) in a suitable solvent (such as, for example, acetone, acetonitrile, pyridine and the like) to afford O-substituted benzoyl-3-propionylsalicylate. Depending upon the solvent used, this intermediate may be isolated therefrom but, in most cases, this is heated, without isolation therefrom, with suitable amount of base (such as, for example, sodium hydride, sodium alkoxide, potassium carbonate, and the like) at 50° to 130° C. for one to eight hours.

Anyway, the resulting 3-(alpha-substituted benzoylpropionyl)salicylate is treated in 1 to 40% ethanolic hydrochloric acid for one to three hours at room temperature or under heating to reflux to afford 3-methylflavone-8-carboxylate derivatives.

Method 5

2-Hydroxy-3-propenylpropiophenone is made to react with substituted benzoic acid chloride or with substituted benzoate at 50° to 100° C. for two to eight hours in the presence of two or more equivalents (preferably 2.1 to 6 equivalents) of base (such as, for example, sodium hydride, sodium alkoxide, and the like) in a suitable solvent (such as, for example, dimethyl formamide, dioxan, tetrahydrofuran and the like) to afford 2-hydroxy-3-propenyl-alpha-substituted benzoyl propiophenone.

This intermediate may alternatively prepared by the following way. Thus, 2-hydroxy-3-propenylpropiophenone is made to react with substituted benzoic acid chloride at −10° C. to room temperature for one to twenty four hours in the presence of suitable amount of base (such as, for example, sodium hydride, sodium alkoxide, potassium carbonate, pyridine, triethylamine and the like) in a suitable solvent (such as, for example, acetone, tetrahydrofuran, dioxane, dimethyl formamide, acetonitrile, pyridine and the like) to give 2-substituted benzoyloxy-3-propenylpropiophenone. This may be isolated therefrom depending upon the kind of the solvent used but, in most cases, it is treated in, without isolating therefrom, a suitable amount of base (such as, for example, sodium hydride, sodium alkoxide, potassium carbonate and the like) at 50° to 130° C. for one to eight hours.

Anyway, the resulting 2-hydroxy-3-propenyl-alpha-substituted benzoyl propiophenone is treated in 1 to 40% ethanolic hydrochloric acid at room temperature or under heating to reflux for one to three hours to afford 3-methyl-8-propenylflavone derivatives. This is oxidized, in a solvent mainly composed of acetic acid, with oxidizing agent such as potassium permanganate or potassium periodate to afford 3-methylflavone-8-carboxylic acid derivatives (II). The acid (II) may be converted to other compounds (III) and (IV) of the invention as follows:

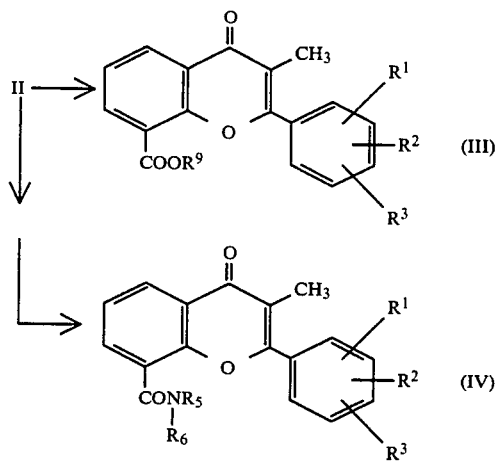

In the formulas, R$^1$, R$^2$, R$^3$, R$^5$ and R$^6$ are the same as already defined and R$^9$ is lower alkyl or (hydroxy) lower alkyl.

3-methylflavone-8-carboxylic acid derivatives (II) as obtained above can be converted to 3-methylfavone-8-carboxylate derivatives (III) by various methods as shown below.

1. Acid halide method

The carboxylic acid (II) which is a starting material or salt thereof is made to react with acid halogenating reagent (such as, for example, thionyl chloride, phosphorus trichloride, phosphorus pentachloride, phosphorus oxychloride, and the like) at 0° to 100° C. for thirty minutes to ten hours in the presence or absence of organic solvent (such as, for example, methylene chloride, chloroform, benzene, toluene, xylene and the like) to afford carboxylic acid halide. The resulting acid halide is made to react with alcohol (such as, for example, methanol, ethanol, propanol, isopropanol, butanol, tertiary butanol and the like) at $-10°$ to $100°$ C. for one to ten hours in a suitable solvent (such as, for example, methylene chloride, chloroform, benzene, toluene, xylene, dioxan, acetone, dimethyl formamide and the like) in the presence, if desired, of base (such as, for example, triethylamine, dimethylaniline, pyridne, sodium hydroxide, potassium hydroxide, potassium carbonate, sodium hydride, and the like) to give 3-methylflavone-8-carboxylic acid esters (III).

2. Direct esterification method

The compound (II) or salt thereof is made to react with alcohol in the presence of an acid catalyst (such as, for example, hydrochloric acid, sulfuric acid and the like) to afford esters. Alternatively, the compound (II) and alcohol are subjected to dehydrative condensation in the presence of a condensation agent (such as, for example, dicyclohexyl carbodiimide, diethyl phosphoryl cyanide, diphenyl phosphoryl azide, and the like) to afford esters (III).

3. Acid anhydride method

The compound (II) is made to react with chlorocarbonates and the resulting mixed acid anhydride is made to react with alcohol to afford esters (III).

4. Activated ester method

The compound (II) is made to react with 2,4-dinitrophenol, N-hydroxysuccinimide and the like and the resulting activated ester is made to react with alcohol to give esters (III).

5. Alkyl halide method

Metal salt of the compound (II) (such as sodium salt, potassium salt, and the like) or amine salt of the compound (II) (such as triethylamine salt and other amine salts) is made to react with alkyl halide to afford esters (III).

Incidentally, 3-methylflavone-8-carboxylic acid (II) can be changed to various 3-methylflavone-8-carboxylic acid amide derivatives (IV) by the following routes.

1. Acid halide method

The carboxylic acid (II) or salt thereof is made to react with acid halogenating agent (such as, for example, thionyl chloride, phorphorous trichloride, phosphorus pentachloride, phosphorus oxychloride, and the like) in the presence or absence of an organic solvent (such as, for example, methylene chloride, chloroform, benzene, toluene, xylene, and the like) at $0°$ to $100°$ C. for thirty minutes to ten hours to afford carboxylic acid halide. The resulting acid halide is made to react with various amines (such as, for example, ammonia, methylamine, ethylamine, propylamine, isopropylamine, butylamine, tertiary butylamine, pentylamine, hexylamine, cyclopentylamine, cyclohexylamine, cycloheptylamine, dimethylamine, ethyl methylamine, diethylamine, methyl propylamine, ethyl propylamine, dipropylamine, butyl methylamine, butyl ethylamine, dibutylamine, pyrrolidine, piperidine, morpholine, thiomorpholine, piperazine, and the like) at $-10°$ to $100°$ C. for one to ten hours in a suitable solvent (such as, for example, methylene chloride, chloroform, benzene, toluene, xylene, dioxane, tetrahydrofuran, acetone, methyl ethyl ketone, dimethyl formamide, and the like) in the presence or absence of base (such as, for example, triethylamine, dimethylaniline, pyridine, sodium hydroxide, potassium hydroxide, potassium carbonate, sodium carbonate, sodium hydride, and the like) to afford 3-methylflavone-8-carboxylc acid amide derivatives (IV).

2. Dehydrative condensation method

The compound (II) or salt thereof is subjected to dehydrative condensation with an amine in the presence of a condensation agent (such as, for example, dicyclohexylcarbodiimide, diethylphosphoryl cyanide, diphenylphosphoryl azide, and the like) to synthesize carboxylic acid amide (IV).

3. Acid anhydride method

The compound (II) or salt thereof is made to react with chlorocarbonate and the like and the resulting mixed acid anhydride is made to react with amine to afford carboxylic acid amide (IV).

4. Activated ester method

The compound (II) is made to react with 2,4-dinitrophenol, N-hydroxysuccinimide and the like to afford activated ester and then made to react with amines to afford carboxylic acid amides (IV).

The 3-Methylflavone derivatives as manufactured above can be easily isolated and purified by conventional methods such as, for example, recrystallization, chromatography and the like.

Among the present invention compounds thus prepared, those in which $R^4$ is hydroxy can be made into salts with conventional pharmaceutically acceptable basic compounds. Examples of such basic compounds are sodium hydroxide, potassium hydroxide, aluminum hydroxide, potassium hydroxide, sodium carbonate, potassium carbonate, sodium bicarbonate, potassium bicarbonate and other inorganic basic compounds, morpholine, piperazine, pyrrolidine, thiomorpholine, methylamine, diethylamine, butyl ethylamine, triethylamine and other organic basic compounds.

The compounds (I) according to the present invention exhibit an antiallergic action and, accordingly, they may be administered to patients suffering from asthma, hay fever, hives, atopic dermatitis, and the like. Further, they exhibit an anti-inflammatory action and, consequently, they may be administered to patents suffering from chronic rheumatoid arthritis, pain after operations, acute upper respiratory inflammations, toothache, dismenorrhea, and the like.

The effect of the compounds (I) of the present invention in the treatment of asthma and allergic diseases were evaluated by a passive cutaneous anaphylaxis assay (PCA) in rats and by measuring anti-SRS-A action using ileus of guinea pigs.

Test Method No. 1 (PCA)

(i) Antiserum abundant in homocytotropic antibody is prepared by the same method as Tada and Okumura did (cf. Journal of Immunology, volume 106, page 1002, 1976). Thus, one mg (calculated as an amount of protein) of DNP-As (2,4-dinitrophenyl-coupled ascaris extract) prepared by methods of Strejan and Campbell (Journal of Immunology, volume 98, page 893, 1971) and of Eisen (Journal of American Chemical Society, volume 85, page 4593, 1953) and $1 \times 10^{-10}$ pertussis vaccine are administered to each paw of Wister strain rats (180 to 200 grams body weights) by dividing the dose by four. Five days later, 0.5 mg of DNP-As is adminstered into muscle of back. Eight days later from the initial immunization, blood is taken from descending aorta under anesthetizing with ether, the resulting serum is stored at −80° C. and is melted before use.

(ii) Effect of tested compounds is investigated as follows:

Anti-serum obtained by the method (i) is diluted with physiological saline solution double by double successively and 0.05 ml of each diluted solution is administered into back of Wister strain rats (140 to 160 grams body weight) subcutaneously. After 72 hours, a solution of 2 mg (calculated as protein) of DNP-As and 2.5 mg of Evand Blue dissolved in 1 ml of physiological saline solution is administered intravenously at a dose of 5 ml/kg. After thirty minutes from antigen solution administration, the animals are killed and diameters of blue spots appeared at the place where antiserum is administered are measured. The PCA test is conducted by the same method as already described using a diluted solutions of antiserum which always show 10 mm or more of spot diameters and the effect of the test compounds is judged. Thus, antiserum diluted solutions are administered to two places in back. Test compounds are administered orally at the dose of 10 mg/kg one hour before administration of antigen solution. From the skin of reacted parts of killed animals, leaked or emitted dyestuff is extracted [cf. Baeck and Steinetz: J. Pharmacol. Exp. Ther., Vol. 131, page 400 (1961)] and the amount of the dyestuff is measured. The inhibition ratio is calculated by the following expression:

$$\text{Inhibition Ratio} = \left(1 - \frac{A'}{A}\right) \times 100$$

in which R' is an amount of dyestuff in the group treated with the test compounds and A is that in the control group.

Anti-SRS-A action (An anti-action against slow reacting substance of anaphylaxie)

Hartley strain male guinea pigs (300 to 350 grams body weight) are killed and 1.0 to 1.5 cm of ileus is immediately excised from ileocecal parts and is suspended in 10 ml of Tyrode solution (95% $O_2$–5% $CO_2$ saturation) containing $10^{-7}$ g/ml of atropine and $10^{-6}$ g/ml of pyrilamine. SRS-A (20 units) (the amount of SRS-A showing the same shrinkage as 5 ng of histamine is defined as one unit) prepared by using sensitized guinea pig lung is given to cause shrinkage there. Then antagonistic action of test compounds treated five minutes ago against the shrinkage is measured and recorded via isotonic transducer.

$$\text{Inhibition Ratio of Test Compd (\%)} = \left(1 - \frac{A'}{A}\right) \times 100$$

in which A' is a height of shrinkage of SRS-A + test compound and A is that of SRS-A.

TABLE 1

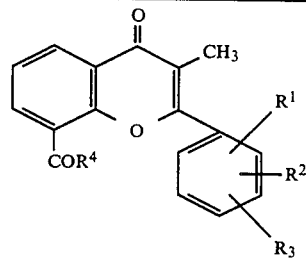

(I)

| Example No. | $R^1, R^2, R^3$ | $R^4$ | PCA Inhibition Ratio % | SRS-A $10^{-6}$ M | Inhibition Ratio % $10^{-7}$ M |
|---|---|---|---|---|---|
| 8 | H | OMe | 17.4 | 64.9 | 45.0 |
| 9 | H | $N(Et)_2$ | 21.9 | 64.7 | 50.7 |
| 11 | 2'-OMe | OEt | 16.3 | 100 | 35.1 |
| 12 | 2'-OMe | $N(Et)_2$ | 19.2 | 52.4 | 8.3 |
| 13 | 2'-OMe | NHEt | 23.0 | 45.2 | 37.4 |
| 15 | 4'-OMe | NHEt | 19.0 | 41.9 | 30.3 |
| 16 | 2'-OEt | OH | 18.6 | 14.8 | 10.4 |
| 17 | 2'-OEt | OEt | 21.1 | 72.5 | 50.0 |
| 18 | 2'-OEt | $N(Et)_2$ | 27.4 | 57.1 | 32.1 |
| 4 | 2'-OEt | $OCH_2CH_2OH$ | 20.5 | 67.2 | 42.4 |
| 19 | 2'-OEt | NHEt | 16.0 | 50.0 | 30.0 |
| 20 | 2'-O—$isoC_3H_7$ | OH | 20.7 | 38.5 | 20.4 |
| 21 | 2'-O—$isoC_3H_7$ | OEt | 17.8 | 31.0 | 19.8 |
| 22 | 2'-O—$isoC_3H_7$ | $N(Et)_2$ | 16.1 | 66.7 | 40.0 |
| 23 | 2',3'-$(OMe)_2$ | OH | 19.5 | 24.0 | 6.2 |
| 24 | 2',3'-$(OMe)_2$ | OEt | 20.4 | 100 | 18.2 |
| 28 | 2',4'-$(OMe)_2$ | $N(Et)_2$ | 20.1 | 63.2 | 23.0 |
| 31 | 3',4',5'-$(OMe)_3$ | OEt | 20.2 | 63.0 | 20.4 |
| 30 | 3',4',5'-$(OMe)_3$ | $N(Et)_2$ | 16.3 | 31.0 | 18.0 |
| 34 | 2'-Me | OEt | 19.5 | 71.4 | 47.6 |
| 35 | 2'-Me | $N(Et)_2$ | 13.3 | 48.8 | 18.0 |
| 37 | 2'-Et | OEt | 20.5 | 100 | 25.0 |
| 38 | 2'-Et | $N(Et)_2$ | 16.0 | 100 | 29.6 |
| 39 | 2',4'-$(Me)_2$ | OH | 37.0 | 5.3 | 3.2 |
| 40 | 2',4'-$(Me)_2$ | OEt | 17.3 | 73.9 | 8.1 |
| 41 | 2',4'-$(Me)_2$ | $N(Et)_2$ | 31.4 | 54.1 | 23.4 |
| 42 | 2',4'-$(Me)_2$ | $OCH_2CH_2OH$ | 19.8 | 27.6 | 10.3 |

TABLE 1-continued (I)

[Structure: 3-methyl-8-(COR⁴)-2-(substituted phenyl)-4H-chromen-4-one with R¹, R², R³ on phenyl ring]

| Example No. | R¹,R²,R³ | R⁴ | PCA Inhibition Ratio % | SRS-A $10^{-6}$ M | Inhibition Ratio % $10^{-7}$ M |
|---|---|---|---|---|---|
| 43 | 2',4'-(Me)₂ | N(Et)(n-C₄H₉) | 18.8 | 68.1 | 23.4 |
| 45 | 4'-Et | OEt | 19.0 | 52.2 | 16.0 |
| 7 | 4'-isoC₃H₇ | OH | 19.7 | 40.8 | 19.0 |
| 48 | 4'-isoC₃H₇ | N(Et)₂ | 27.2 | 100 | 23.3 |
| 49 | 4'-isoC₃H₇ | N(n-C₄H₉)₂ | 20.0 | 82.8 | 55.6 |
| 50 | 4'-isoC₃H₇ | N(Et)(n-C₄H₉) | 21.4 | 100 | 70.0 |
| 51 | 4'-isoC₃H₇ | NHEt | 19.0 | 75.0 | 17.5 |
| 52 | 4'-isoC₃H₇ | NH(n-C₆H₁₃) | 13.5 | 66.1 | 20.7 |
| 53 | 4'-isoC₃H₇ | NH(cycloC₆H₁₁) | 10.3 | 51.9 | 40.0 |
| 54 | 4'-isoC₃H₇ | N-piperidyl | 13.0 | 69.0 | 38.6 |
| 55 | 4'-tertC₄H₉ | OH | 20.3 | 100 | 21.1 |
| 56 | 4'-tertC₄H₉ | OEt | 20.2 | 44.9 | 19.0 |
| 57 | 4'-tertC₄H₉ | N(Et)₂ | 19.1 | 39.1 | 10.4 |
| 58 | 4'-n-C₅H₁₁ | OH | 28.8 | 40.0 | 10.3 |
| 59 | 4'-n-C₅H₁₁ | OEt | 19.4 | 38.1 | 9.8 |
| 60 | 4'-n-C₅H₁₁ | N(Et)₂ | 13.4 | 100 | 44.9 |
| 61 | 4'-n-C₅H₁₁ | ONa | 22.7 | 40.7 | 9.4 |
| 62 | 4'-n-C₈H₁₇ | OH | 16.3 | 83.3 | 31.0 |
| 67 | 2'-Cl | OEt | 19.8 | 100 | 42.9 |
| 68 | 2'-Cl | N(Et)₂ | 21.1 | 55.3 | 9.8 |
| 69 | 2'-Cl | OCH₂CH₂OH | 14.3 | 55.3 | 9.8 |
| 71 | 4'-Cl | OEt | 36.9 | 10.3 | 6.0 |
| 72 | 4'-Cl | N(Et)₂ | 16.3 | 42.1 | 7.5 |
| 73 | 4'-Cl | NHEt | 19.4 | 29.4 | 6.2 |
| 74 | 4'-Cl | OCH₂CH₂OH | 17.3 | 52.0 | 18.7 |
| 76 | 2',5'-(Cl)₂ | OH | 13.2 | 65.2 | 40.0 |
| 77 | 2',5'-(Cl)₂ | OEt | 16.3 | 67.4 | 6.9 |
| 78 | 2',5'-(Cl)₂ | N(Et)₂ | 26.3 | 79.3 | 5.6 |
| 80 | 2',4'-(Cl)₂ | OEt | 21.3 | 61.7 | 17.6 |
| 81 | 2',4'-(Cl)₂ | N(Et)₂ | 20.4 | 57.1 | 9.8 |

Anti-inflammatory action was evaluated by measuring the effect of the compounds (I) in inhibiting carrageenin edema as illustrated below.

Carrageenin edema in hind foot of rat.

Experimental method

SD strain rats of about 150 grams body weight were used; each group consisted of five rats. Thus, 0.1 ml of 0.5% carrageenin solution in physiological saline water was hypodermically injected to the right hind foot of rat. The test compound was given orally to rats one hour prior to the above carrageenin treatment. Then the volume of the foot before and three hours after the carrageenin treatment was measured and the difference was compared with that of the control group.

| Compound of Example Numbers | % Inhibition |
|---|---|
| 35 | 13.0 |
| 48 | 23.2 |
| 58 | 31.9 |
| 20 | 32.5 |
| 4 | 33.9 |
| 55 | 19.1 |
| Acetylsalicyclic Acid (control) | |

Acute toxicity is observed for two weeks by oral adminsitration of 4000 mg/kg of the test compounds to male mice. One group consists of four mice. Numbers of dead mice are shown in numerators.

| Example Number | Lethal Ratio |
|---|---|
| 4 | 0/4 |
| 11 | 0/4 |
| 13 | ¼ |
| 18 | 0/4 |
| 48 | 0/4 |
| 58 | 0/4 |
| 62 | 0/4 |
| 74 | 0/4 |

Lethal ratios of all other compounds are 0/4 by oral administration of 300 mg/kg.

The compounds (I) of the invention are used to treat allergic diseases, asthma and inflammation in human and non-human mammals by administering to the sufferer an effective amount of the compound (I) of the invention, preferably in the form of a pharmaceutical composition comprising an effective amount of the compound (I) in combination with a pharmaceutically acceptable, nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

The compounds of the present invention may be used for the treatment of allergic diseases, such as asthma, as follows: by oral administration, 1 to 1000 mg, one to three times daily; by rectal administration, 1 to 500 mg, one to three times daily; by inhalation, 0.1 to 100 mg, two to three times daily; by intravenous administration, 0.1 to 50 mg, three to four times daily; by nasal administration, 0.1 to 100 mg, two to three times daily; by eye drops, 0.1 to 50 mg, three to four times daily; as an ointment, 1 to 100 mg, two to three times daily.

The compounds of the invention may be used for the treatment of inflammation as follows; for oral administration, 10 to 800 mg, one to three times daily; by rectal administration, 5 to 500 mg, one to three times daily; by intravenous administration, 0.1 to 50 mg, three to four times daily; as an ointment, 1 to 100 mg, two to three times daily.

The dosages and dosage regimens are set forth above for human adults. However, the dosage regimen must in each case be carefully adjusted, utilizing sound professional judgement and considering the age, weight and condition of the recipient, the route of administration and the nature and gravity of the illness. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free-flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of nontoxic alcoholic vehicles. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or deaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories, in which the compound is admixed with low-melting, water-soluble or insoluble solids such as polyethylene glycol, cocoa butter, higher esters as for example myristyl palmitate, or mixtures thereof. Rectal gelatin capsules containing a suspension of the compound in a vegetable oil may also be used.

Compositions suitable for administration by inhalation may be in the form of a solution of the compound in a pharmaceutically acceptable liquid or an aerosol solution containing the compound. Accordingly, the inhalant composition may be administered by an intermittent positive pressure breathing apparatus, a hand bulb nebulizer or a metered dose inhaler, as is conventional for inhalant compositions. A suitable inhalant composition may take the form of a solution comprising the compound, an inert propellant, such as dichlorodifluoromethane and/or dichlorotetrafluoroethane and the like, a preservative and a liquid solvent, such as aqueous alcohol. Another suitable form of the composition is a microcrystalline suspension comprising the compound, inert propellants and oleic acid.

While the routes of administration of the compound of the invention include oral, parenteral (i.e., intramuscular, intraperitoneal and intravenous), rectal, and by inhalation, oral administration is particularly preferred.

The preferred pharmaceutical compositions are therefore those in a form suitable for oral administration, such as tablets and liquids.

It is desirable that about 0.1 to 99%, preferably 0.5 to 90%, of one or more of the compounds of the present invention, is contained in the pharmaceutical composition.

Examples of pharmaceutical compositions according to the present invention, are as follows.

EXAMPLES FOR PHARMACEUTICAL COMPOSITIONS (1) Capsules containing beta-hydroxyethyl 2-ethoxy-3-methyl-flavone-8-carboxylate (compound of Example 4) as a main constituent.

The compound of Example 4 and diluents are uniformly mixed as per the following ratios and filled in hard gelatin capsules.
Compound of Example 4: 50 mg
Hydroxypropylcellulose of low degree of substitution: 20 mg
Lactose: 84 mg
Potato starch: 40 mg
Talc: 5 mg
Magnesium stearate: 1 mg
Mixed to make: 200 mg per capsule (2) Tablets mainly composed of 2',3,4'-trimethylflavone-8-carboxylic acid N,N-diethylamide (the compound of Example 41).

A mixture of 100 mg of pulverized compound (of Example 41), 100 mg of lactose, 75 mg of crystalline cellulose and 40 mg of potato starch is mixed, kneaded after addition of binding agent solution prepared from 10 mg of polyvinyl alcohol, the mixture is passed through a sieve of 16 mesh to make granulated, dried, and passed through a sieve of 16 mesh once again to make the size of granules uniform. The granules are then mixed with 3 mg of magnesium stearate and 7 mg of talc and compressed into tablets. The resulting tablets may, if necessary, be coated with conventional coating base or with sucrose and the like.

The present invention is further illustrated by way of the following Reference Examples and Examples.

REFERENCE EXAMPLE 1

A mixture of 225 grams of 2-hydroxypropiophenone, 247 grams of allyl bromide, 415 grams of potassium carbonate and 5 grams of potassium iodide is heated to reflux for twenty four hours in 1 liter of acetone. After cooled, insoluble matters are removed by filtration, the filtrate is concentrated, the residue is dissolved in benzene, and the solution is washed with 10% sodium hydroxide solution. After washing with water, the solution is dried with anhydrous magnesium sulfate and benzene is evaporated therefrom. The resulting oil is distilled in vacuo to give 266 grams of 2-allyloxypropiophenone, colorless oil, b.p. 120° to 124° C.

2-Allyloxypropiophenone (266 grams) is heated at 230° to 240° C. for six hours to conduct Claisen rearrangement. Then it is distilled in vacuo to give 233 grams of 3-allyl-2-hydroxypropiophenone, pale yellow oil, b.p. 112° to 115° C.

Then to 233 grams of 3-allyl-2-hydroxypropiophenone are added 212 grams of potassium hydroxide, 200 ml of methanol and 1100 ml of n-butanol and the mixture is heated to reflux for twenty four hours. It is then poured into ice water, acidified with concentrated hydrochloric acid, crystals separated out therefrom are collected by filtration, washed with water and recrystallized from methanol to give 105 grams of 2-hydroxy-3-propenylpropiophenone, yellow needles, melting point 83° to 85° C.

EXAMPLE 1

4'-Methoxy-3-methylflavone-8-carboxylic acid

To 2.47 grams of 2-hydroxy-3-propenylpropiophenone are added 6.65 grams of p-methoxybenzoyl chloride and one half of 6.88 grams of anhydrous sodium p-methoxybenzoate, the mixture is heated in a nitrogen stream and, when 2-hydroxy-3-propenyl-propipheone is dissolved, the residue of anhydrous sodium p-methoxybenzoate is added thereto, and the mixture is stirred at 180° to 190° C. for five hours. After cooled, the mixture is dissolved in ethyl acetate, the solution is washed with 10% sodium hydroxide solution and with water, and dried with anhydrous magnesium sulfate and finally the solvent is evaporated therefrom to give 3.0 grams of 4'-methoxy-3-methyl-8-propenylflavone, colorless needles, melting point 169° to 171° C.

4'-Methoxy-3-methyl-8-propenylflavone (3 grams) is dissolved in 35 ml of glacial acetic acid, small amount of ice is added thereto, 6.8 grams of potassium permanganate is added thereto during eight hours keeping the solution at 20° to 30° C. and stirring throughout, then aqueous solution of sodium bisulfite is added thereto keeping the solution at 30° to 40° C., and the mixture is stirred for one hour. Crystals separated out therefrom are collected by filtration, washed with water, then dissolved in 10% sodium hydroxide solution, the solution is treated with an activated charcoal, filtered, the filtrate is adjusted to pH 3 with concentrated hydrochloric acid, crystals separated out are collected by filtration, and washed with water to give 1.2 grams of 4′-methoxy-3-methylflavone-8-carboxylic acid, colorless needles, melting point 266° to 267° C.

Elementary analysis calculated for $C_{18}H_{14}O_5$: C 69.67, H 4.54; Found: C 69.74, H 4.35.

EXAMPLE 2

Ethyl 4′-methoxy-3-methylflavone-8-carboxylate

To 3 grams of 4′-methoxy-3-methylflavone-8-carboxylic acid is added 100 ml of 35% ethanolic hydrochloric acid, the mixture is heated to reflux for four hours, the solvent is evaporated therefrom, the residue is dissolved in ethyl acetate, the solution is washed with 10% sodium hydroxide solution, then with water, and dried with anhydrous magnesium sulfate. The solvent is evaporated therefrom and the residue is recrystallized from a mixture of benzene and n-hexane to give 2.7 grams of ethyl 4′-methoxy-3-methylflavone-8-carboxylate, colorless needles, melting point 137° to 139° C.

Elementary analysis calculated for $C_{20}H_{18}O_5$: C 70.99, H 5.36; Found: C 71.11, H 5.44.

EXAMPLE 3

4′-Methoxy-3-methylflavone-8-carboxylic acid N,N-diethylamide.

To 1.8 grams of 4′-methoxy-3-methylflavone-8-carboxylic acid is added 20 ml of thionyl chloride and the mixture is stirred at room temperature for seven hours. Thionyl chloride is evaporated therefrom, the residue is dissolved in 50 ml of chloroform, and 10 ml of diethylamine is dropped thereinto with ice cooling. The mixture is stirred at room temperature for two hours, washed with 10% hydrochloric acid, then with 10% sodium hydroxide solution, finally washed with water, and dried with anhydrous magnesium sulfate. The solvent is evaporated therefrom and the residue is recrystallized from a mixture of benzene and n-hexane to give 2.0 grams of 4′-methoxy-3-methylflavone-8-carboxylic acid N,N-diethylamide, colorless needles, melting point 143° to 147° C.

Elementary analysis calculated for $C_{22}H_{23}O_4$: C 72.30, N 6.34; Found: C 72.48, N 6.18.

EXAMPLE 4

Beta-Hydroxyethyl 2′-ethoxy-3-methylflavone 8-carboxylate.

One gram of 2′-ethoxy-3-methylflavone-8-carboxylic acid prepared by the same way as Example 1 is dissolved in 30 ml of dimethyl formamide, 0.5 gram of anhydrous potassium carbonate is added thereto, 2 grams of ethylene bromohydrin is dropped thereinto with stirring, and the mixture is stirred at 50° C. for four hours. Then it is poured into ice water, the mixture is neutralized with 10% hydrochloric acid, extracted with ethyl acetate, the extract is washed with water, dried with anhydrous magnesium sulfate, the solvent is evaporated therefrom, and the residue is recrystallized from a mixture of benzene and n-hexane to give 0.8 gram of beta-hydroxyethyl 2′-ethoxy-3-methylflavone-8-carboxylate, colorless needles, melting point 143° to 144.5° C.

Elementary analysis calculated for $C_{21}H_{20}O_6$: C 68.46, H 5.47; Found: C 68.62, H 5.42.

EXAMPLE 5

Sodium 2′,3,4′-trimethylflavone-8-carboxylate

One gram of 2′,3,4′-trimethylflavone-8-carboxylic acid prepared by the same way as Example 1 is dissolved in methanol, equimolar 2N sodium hydroxide solution is added thereto, methanol is evaporated therefrom, the residue is dissolved in small amount of water, the solution is lyophilized, and 1.0 gram of sodium 2′,3,4′-trimethylflavone-8-carboxylate, colorless powder, melting point 218° to 220° C., is obtained.

Elementary analysis calculated for $C_{19}H_{15}O_4Na$: C 69.08, H 4.57; Found: C 68.87, H 4.64.

EXAMPLE 6

N-n-Butyl-N-ethylamine salt of 4′-chloro-3-methylflavone-8-carboxylic acid

Two grams of 4′-chloro-3-methylflavone-8-carboxylic acid prepared by the same way as Example 1 is dissolved in 100 ml of chloroform. Butyl ethylamine (0.65 gram) is added thereto, then chloroform is evaporated therefrom and the residue is recrystallized from ethanol to give 2.2 grams of N-n-butyl-N-ethylamine salt of 4′-chloro-3-methylflavone-8-carboxylic acid, colorless flakes, melting point 184° to 189° C.

Elementary analysis calculated for $C_{23}H_{26}ClNO_4$: C 66.41, H 6.30, N 3.36; Found: C 66.36, H 6.38, N 3.26.

EXAMPLE 7

4′-Isopropyl-3-methylflavone-8-carboxylic acid

2-Hydroxy-3-propenylpropiophenone (2.4 grams) is dissolved in 30 ml of dimethylformamide and 0.6 gram of 50% sodium hydride is added thereto little by little at room temperature with stirring. The mixture is stirred for one hour more at the same temperature and 2.4 grams of p-isopropylbenzoyl chloride is dropped thereinto with ice cooling. The mixture is stirred at room temperature for one hour, 0.6 gram of 50% sodium hydride is added thereto, the mixture is heated at 60° to 70° C. for one hour, cooled, and poured into ice water. This is extracted with ethyl acetate, the extract is washed with water, dried with anhydrous magnesium sulfate, the solvent is evaorated therefrom, and the resulting crystals are washed with n-hexane to give 3.6 grams of 2-hydroxy-3-propenyl-alpha-p-isopropylbenzoylpropiophenone, pale yellow powder, melting point 108° to 110° C.

To 3.6 grams of the resulting 2-hydroxy-3-propenyl-alpha-p-isopropylbenzoulpropiophenone is added 10 ml of 40% ethanolic hydrochloric acid and the mixture is allowed to stand at room temperature for thirty minutes. This is poured into ice water, the mixture is neutralized with aqueous solution of sodium bicarbonate, extracted with ethyl acetate, the extract is washed with water, dried with anhydrous magnesium sulfate, the solvent is evaporated therefrom, the residue is washed with methanol and recrystallized from methanol to give 3.4 grams of 4′-isopropyl-3-methyl-8-propenylflavone, colorless prisms, melting point 105° to 107° C.

4′-Isopropyl-3-methyl-8-propenylflavone (3.4 grams) is dissolved in 40 ml of glacial acetic acid, small amount of water is added thereto, 6.6 grams of potassium permanganate is added thereto during eight hours with stirring keeping the inner temperature at 20° to 30° C., then aqueous solution of sodium bisulfite is added thereto keeping the inner temperature at 30° to 40° C., and the mixture is stirred for one hour. Crystals separated out therefrom are collected by filtration, washed with water, dissolved in 10% sodium hydroxide solution, the solution is treated with activated charcoal, filtered, and the filtrate is adjusted to pH 3 with concentrated hydrochloric acid, crystals separated out are collected by filtration, washed with water and recrystallized from methanol to give 1.9 grams of 4'-isopropyl-3-methylflavone-8-carboxylic acid, colorless prisms, melting point 216° to 220° C.

Elementary analysis calculated for $C_{20}H_{18}O_4$: C 74.51, H 5.62; Found: C 74.44, H 5.63.

Compounds of Examples 8 to 81 are sythesized by the same way as described for the compounds of Examples 1 to 7. They are given in the following tables.

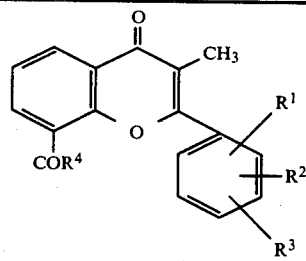
(I)

| Example No | $R^1, R^2, R^3$ | $R^4$ | Appearance | M.P. (°C.) | Exptl. Formula | Elementary Analysis (%) [Upper Column: Calcd / Lower Column: Found] |
|---|---|---|---|---|---|---|
| 8 | H | OMe | Colorless needles | 173~176 | $C_{18}H_{14}O_4$ | C 73.45 H 4.79 / C 73.54 H 4.53 |
| 9 | H | $N(Et)_2$ | Colorless crystals | 164~169 | $C_{21}H_{21}NO_3$ | C 75.20 H 6.31 N 4.17 / C 75.41 H 6.34 N 4.10 |
| 10 | 2'-OMe | OH | Colorless needles | 238~240 | $C_{18}H_{14}O_5$ | C 69.67 H 4.54 / C 69.67 H 4.45 |
| 11 | 2'-OMe | OEt | Colorless needles | 91~93 | $C_{20}H_{18}O_5$ | C 70.99 H 5.36 / C 71.16 H 5.10 |
| 12 | 2'-OMe | $N(Et)_2$ | Colorless crystals | 169~174 | $C_{22}H_{23}NO_4$ | C 72.30 H 6.34 N 3.83 / C 72.09 H 6.29 N 3.78 |
| 13 | 2'-OMe | NHEt | Colorless needles | 178~179 | $C_{20}H_{19}NO_4$ | C 71.20 H 5.67 N 4.15 / C 71.05 H 5.67 N 4.10 |
| 14 | 3'OMe | OH | Colorless needles | 228~229 | $C_{18}H_{14}O_5$ | C 69.67 H 4.54 / C 69.57 H 4.41 |
| 15 | 4'-OMe | NHEt | Colorless needles | 217~221 | $C_{20}H_{19}NO_4$ | C 71.20 H 5.67 N 4.15 / C 71.30 H 5.70 N 4.03 |
| 16 | 2'-OEt | OH | Colorless needles | 213~215 | $C_{19}H_{16}O_5$ | C 70.36 H 4.97 / C 70.34 H 5.00 |
| 17 | 2'-OEt | OEt | Colorless crystals | 118~120 | $C_{21}H_{20}O_5$ | C 71.57 H 5.72 / C 71.82 H 5.64 |
| 18 | 2'-OEt | $N(Et)_2$ | Colorless crystals | 110~113 | $C_{23}H_{25}NO_4$ | C 72.80 H 6.64 N 3.69 / C 72.83 H 6.67 N 3.66 |
| 19 | 2'-OEt | NHEt | Colorless needles | 154~157 | $C_{21}H_{21}NO_4$ | C 71.77 H 6.02 N 3.98 / C 71.93 H 6.19 N 3.85 |
| 20 | 2'-O—$isoC_3H_7$ | OH | Colorless crystals | 222~225 | $C_{20}H_{18}O_5$ | C 70.99 H 5.36 / C 71.09 H 5.43 |
| 21 | 2'-O—$isoC_3H_7$ | OEt | Colorless crystals | 103~104 | $C_{22}H_{22}O_5$ | C 72.11 H 6.05 / C 72.20 H 6.08 |
| 22 | 2'-O—$3H_7$ | $N(Et)_2$ | Colorless crystals | 129~133 | $C_{24}H_{27}NO_4$ | C 73.25 H 6.91 N 3.55 / C 73.11 H 6.86 N 3.46 |
| 23 | 2',3'-$(OMe)_2$ | OH | Colorless crystals | 255~260 | $C_{19}H_{16}O_6$ | C 67.05 H 4.73 / C 67.07 H 4.63 |
| 24 | 2',3'-$(OMe)_2$ | OEt | Pale yellow needles | 109~113.5 | $C_{21}H_{20}O_6$ | C 68.46 H 5.47 / C 68.72 H 5.20 |
| 25 | 3',4'-$(OMe)_2$ | OH | Pale yellow needles | 273~274 | $C_{19}H_{16}O_6$ | C 67.05 H 4.73 / C 67.31 H 4.58 |
| 26 | 2',4'-$(OMe)_2$ | OH | Colorless crystals | 213~216 | $C_{19}H_{16}O_6$ | C 67.05 H 4.73 / C 67.13 H 4.66 |
| 27 | 2',4'-$(OMe)_2$ | OEt | Colorless needles | 145~149.5 | $C_{21}H_{20}O_6$ | C 68.46 H 5.47 / C 68.69 H 5.51 |
| 28 | 2',4'-$(OMe)_2$ | $N(Et)_2$ | Colorless crystals | 194~198 | $C_{23}H_{25}NO_5$ | C 69.85 H 6.37 N 3.54 / C 69.99 H 6.36 N 3.37 |
| 29 | 2',3',4'-$(OMe)_3$ | OH | Colorless needles | 215~218 | $C_{20}H_{18}O_7$ | C 64.86 H 4.90 / C 64.98 H 4.86 |
| 30 | 2',3',4'-$(OMe)_3$ | $N(Et)_2$ | Colorless needles | 154~157 | $C_{24}H_{27}NO_6$ | C 67.75 H 6.40 N 3.29 / C 67.53 H 6.49 N 3.18 |
| 31 | 2',3',4'-$(OMe)_3$ | OEt | Colorless crystals | 141~143 | $C_{22}H_{22}O_7$ | C 66.32 H 5.57 / C 66.34 H 5.56 |
| 32 | 3',4',5'-$(OMe)_3$ | OH | Colorless needles | 263~265 | $C_{20}H_{18}O_7$ | C 64.86 H 4.90 / C 64.88 H 4.94 |
| 33 | 2'-Me | OH | Colorless crystals | 256.5~258 | $C_{18}H_{14}O_4$ | C 73.45 H 4.79 / C 73.58 H 4.59 |
| 34 | 2'-Me | OEt | Colorless needles | 98~101 | $C_{20}H_{18}O_4$ | C 74.51 H 5.62 / C 74.68 H 5.52 |

-continued

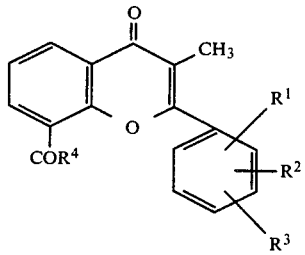

(I)

| Example No | $R^1, R^2, R^3$ | $R^4$ | Appearance | M.P. (°C.) | Exptl. Formula | Elementary Analysis (%) [Upper: Calcd / Lower: Found] |
|---|---|---|---|---|---|---|
| 35 | 2'-Me | $N(Et)_2$ | Pale yellow needles | 134~136 | $C_{22}H_{23}NO_3$ | C 75.62 H 6.63 N 4.00 / C 75.71 H 6.54 N 3.95 |
| 36 | 2'-Et | -Et OH | Colorless crystals | 203~207 | $C_{19}H_{16}O_4$ | C 74.01 H 5.23 / C 74.18 H 5.21 |
| 37 | 2'-Et | OEt | Colorless oil | — | $C_{21}H_{20}O_4$ | C 74.98 H 5.99 / C 74.89 H 5.99 |
| 38 | 2'-Et | $N(Et)_2$ | Pale brown crystals | 117~120 | $C_{23}H_{25}NO_3$ | C 76.00 H 6.93 N 3.85 / C 76.25 H 6.96 N 3.85 |
| 39 | 2',4'-$(Me)_2$ | OH | Colorless crystals | 217~219 | $C_{19}H_{16}O_4$ | C 74.01 H 5.23 / C 73.92 H 5.19 |
| 40 | 2',4'-$(Me)_2$ | OEt | Colorless crystals | 90~92 | $C_{21}H_{20}O_4$ | C 74.98 H 5.99 / C 75.16 H 5.88 |
| 41 | 2',4'-$(Me)_2$ | $N(Et)_2$ | Colorless crystals | 108~111 | $C_{23}H_{25}NO_3$ | C 76.00 H 6.93 N 3.85 / C 76.25 H 6.65 N 3.98 |
| 42 | 2',4'-$(Me)_2$ | $OCH_2CH_2OH$ | Colorless crystals | 113~115 | $C_{21}H_{20}O_5$ | C 71.57 H 5.72 / C 71.57 H 5.64 |
| 43 | 2',4'-$(Me)_2$ | N(Et)(n-$C_4H_9$) | Pale yellow crystals | 110~112 | $C_{25}H_{29}NO_3$ | C 76.69 H 7.46 N 3.57 / C 76.44 H 7.65 N 3.62 |
| 44 | 4'-Et | OH | Yellow crystals | 228~229.5 | $C_{19}H_{16}O_4$ | C 74.01 H 5.23 / C 74.14 H 5.24 |
| 45 | 4'-Et | OEt | Yellow needles | 75~76.5 | $C_{21}H_{20}O_4$ | C 74.98 H 5.99 / C 75.06 H 6.07 |
| 46 | 4'-Et | $N(Et)_2$ | Colorless crystals | 145~147 | $C_{23}H_{25}NO_3$ | C 76.00 H 6.93 N 3.85 / C 75.86 H 6.96 N 3.79 |
| 47 | 4'-iso$C_3H_7$ | OEt | Colorless needles | 57~59 | $C_{22}H_{22}O_4$ | C 75.40 H 6.32 / C 75.48 H 6.38 |
| 48 | 4'-iso$C_3H_7$ | $N(Et)_2$ | Pale brown crystals | 136~139 | $C_{24}H_{27}NO_3$ | C 76.36 H 7.20 N 3.71 / C 76.42 H 7.31 N 3.56 |
| 49 | 4'-iso$C_3H_7$ | $N(n-C_4H_9)_2$ | Colorless crystals | 104~106 | $C_{28}H_{35}NO_3$ | C 77.56 H 8.13 N 3.23 / C 77.50 H 8.09 N 3.39 |
| 50 | 4'-iso$C_3H_7$ | N(Et)(n-$C_4H_9$) | Pale brown crystals | 113~115.5 | $C_{26}H_{31}NO_3$ | C 77.00 H 7.70 N 3.45 / C 77.17 H 7.49 N 3.50 |
| 51 | 4'-iso-$C_3H_7$ | NHEt | Colorless crystals | 162~165 | $C_{22}H_{23}NO_3$ | C 75.62 H 6.63 N 4.00 / C 75.44 H 6.62 N 3.96 |
| 52 | 4'-iso-$C_3H_7$ | NH(n-$C_6H_{13}$) | Colorless crystals | 146~148 | $C_{26}H_{31}NO_3$ | C 77.00 H 7.70 N 3.45 / C 77.06 H 7.85 N 3.65 |
| 53 | 4'iso-$C_3H_7$ | NH-cyclohexyl | Colorless crystals | 195~196.5 | $C_{26}H_{29}NO_3$ | C 77.38 H 7.24 N 3.47 / C 77.54 H 7.34 N 3.54 |
| 54 | 4'-iso-$C_3H_7$ | N-piperidino | Pale brown crystals | 162~165 | $C_{25}H_{27}NO_3$ | C 77.09 H 6.98 N 3.59 / C 77.27 H 6.99 N 3.75 |
| 55 | 4'-tert-$C_4H_9$ | OH | Yellow crystals | 221~224 | $C_{21}H_{20}O_4$ | C 74.98 H 5.99 / C 75.05 H 6.04 |
| 56 | 4'-tert-$C_4H_9$ | OEt | Colorless | 97~99 | $C_{23}H_{24}O_4$ | C 75.80 H 6.63 |

-continued

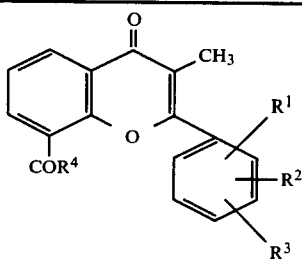

(I)

| Example No | R¹,R²,R³ | R⁴ | Appearance | M.P. (°C.) | Exptl. Formula | Elementary Analysis (%) Upper Column: Calcd / Lower Column: Found |
|---|---|---|---|---|---|---|
| 57 | 4'-tert-$C_4H_9$ | $N(Et)_2$ | Colorless crystals | 145~148 | $C_{25}H_{29}NO_3$ | C 75.85 H 6.73<br>C 76.69 H 7.46 N 3.57 |
| 58 | 4'-n-$C_5H_{11}$ | OH | Colorless crystals | 202~206 | $C_{22}H_{22}O_4$ | C 76.78 H 7.59 N 3.67<br>C 75.40 H 6.32<br>C 75.35 H 6.14 |
| 59 | 4'-n-$C_5H_{11}$ | OEt | Colorless needles | 41~42 | $C_{24}H_{26}O_4$ | C 76.16 H 6.92<br>C 76.07 H 6.76 |
| 60 | 4'-n-$C_5H_{11}$ | $N(Et)_2$ | Colorless crystals | 102~103 | $C_{26}H_{31}NO_3$ | C 77.00 H 7.70 N 3.45<br>C 76.79 H 7.68 N 3.47 |
| 61 | 4'-n-$C_5H_{11}$ | ONa | White powder | 278~286 | $C_{22}H_{21}O_4Na$ | C 70.95 H 5.68<br>C 70.69 H 5.76 |
| 62 | 4'-n-$C_8H_{17}$ | OH | Pale crystals | 182~184 | $C_{25}H_{28}O_4$ | C 76.50 H 7.19<br>C 76.51 H 7.11 |
| 63 | 4'-n-$C_8H_{17}$ | OEt | Colorless oil | — | $C_{27}H_{32}O_4$ | C 77.11 H 7.66<br>C 77.10 H 7.78 |
| 64 | 4'-n-$C_8H_{17}$ | $N(Et)_2$ | Colorless oil | — | $C_{29}H_{37}NO_3$ | C 77.81 H 8.33 N 3.12<br>C 77.68 H 8.43 N 3.11 |
| 65 | 4'-n-$C_8H_{17}$ | NHEt | Colorless crystals | 128~129.5 | $C_{29}H_{33}NO_3$ | C 77.29 H 7.92 N 3.33<br>C 77.14 H 7.94 N 3.46 |
| 66 | 2'-Cl | OH | Colorless crystals | 281~284 | $C_{17}H_{11}ClO_4$ | C 64.87 H 3.52<br>C 64.92 H 3.32 |
| 67 | 2'-Cl | OEt | Colorless crystals | 80.5~82.5 | $C_{19}H_{15}ClO_4$ | C 66.57 H 4.41<br>C 66.77 H 4.22 |
| 68 | 2'-Cl | $N(Et)_2$ | Colorless crystals | 165~168 | $C_{21}H_{20}ClNO_3$ | C 68.19 H 5.45 N 3.78<br>C 68.32 H 5.51 N 3.66 |
| 69 | 2'-Cl | $OCH_2CH_2OH$ | Colorless crystals | 97.5~99.5 | $C_{19}H_{15}ClO_5$ | C 63.60 H 4.21<br>C 63.47 H 4.38 |
| 70 | 4'-Cl | OH | Colorless crystals | 259~260.5 | $C_{17}H_{11}ClO_4$ | C 64.87 H 3.52<br>C 65.01 H 3.44 |
| 71 | 4'-Cl | OEt | Pale yellow crystals | 136~139 | $C_{19}H_{15}ClO_4$ | C 66.57 H 4.41<br>C 66.86 H 4.13 |
| 72 | 4'-Cl | $N(Et)_2$ | Colorless crystals | 162~164.5 | $C_{21}H_{20}ClNO_3$ | C 68.19 H 5.45 N 3.78<br>C 68.28 H 5.36 N 3.67 |
| 73 | 4'-Cl | NHEt | Colorless needles | 249~251 | $C_{19}H_{16}ClNO_3$ | C 66.76 H 4.71 N 4.09<br>C 67.76 H 4.74 N 3.95 |
| 74 | 4'-Cl | $OCH_2CH_2OH$ | Colorless crystals | 184~187 | $C_{19}H_{15}ClO_5$ | C 63.60 H 4.21<br>C 63.78 H 4.11 |
| 75 | 4'-Cl | $OH.Et_3N$ | Colorless prisms | 141~145 | $C_{23}H_{26}ClNO_4$ | C 66.41 H 6.30 N 3.36<br>C 66.53 H 6.33 N 3.48 |
| 76 | 2',5'-$(Cl)_2$ | OH | Colorless crystals | 300 | $C_{17}H_{10}Cl_2O_4$ | C 58.47 H 2.88<br>C 58.48 H 2.73 |
| 77 | 2',5'-$(Cl)_2$ | OEt | Colorless crystals | 85~88.5 | $C_{19}H_{14}Cl_2O_8$ | C 60.49 H 3.74<br>C 60.74 H 3.58 |
| 78 | 2',5'-$(Cl)_2$ | $N(Et)_2$ | Pale brown crystals | 185~187 | $C_{21}H_{19}Cl_2NO_3$ | C 62.38 H 4.73 N 3.46<br>C 62.62 H 4.67 N 3.30 |
| 79 | 2',4'-$(Cl)_2$ | OH | Colorless crystals | 253.5~255 | $C_{17}H_{10}Cl_2O_4$ | C 58.47 H 2.88<br>C 58.66 H 2.70 |
| 80 | 2',4'-$(Cl)_2$ | OEt | Pale brown crystals | 82~84 | $C_{19}H_{14}Cl_2O_4$ | C 60.49 H 3.74<br>C 60.57 H 3.66 |
| 81 | 2',4'-$(Cl)_2$ | $N(Et)_2$ | Pale brown crystals | 164~167 | $C_{21}H_{19}Cl_2NO_3$ | C 62.38 H 4.73 N 3.46<br>C 62.55 H 4.67 N 3.45 |

What is claimed:

1. A compound of the formula (I):

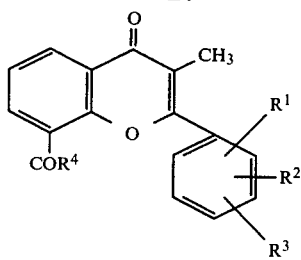

(I)

wherein $R^1$, $R^2$ and $R^3$ are the same or different and are hydrogen, halogen, alkyl of 1 to 15 carbon atoms in total and 1 to 10 carbon atoms in the longest chain, or lower alkoxy; $R^4$ is hydroxy, lower alkoxy, (hydroxy)-lower alkoxy or

wherein $R^5$ is hydrogen or lower alkyl and $R^6$ is lower alkyl or cycloalkyl of 5 to 7 carbon atoms, or $R^5$ and $R^6$ together with the nitrogen atom to which they are attached form pyrrolidino, piperidino, or morpholino; and, when $R^4$ is hydroxy, pharmaceutically acceptable salts thereof, provided that when $R_1$, $R_2$ and $R_3$ are each hydrogen, $R^4$ is other than hydroxy or lower alkoxy.

2. The compound according to claim 1, wherein $R^1$, $R^2$ and $R^3$ are the same or different and are hydrogen, halogen, lower alkyl or lower alkoxy.

3. The compound according to claim 1, wherein $R^4$ is

wherein $R^5$ is hydrogen or lower alkyl and $R^6$ is lower alkyl, or $R^5$ and $R^6$ together with the nitrogen atom to which they are attached form pyrrolidino, piperidino or morpholino.

4. The compound according to claim 1, wherein $R^1$ and $R^2$ are hydrogen, $R^3$ is 2'-ethoxy and $R^4$ is $\beta$-hydroxy-ethoxy.

5. The compound according to claim 1, wherein $R^1$ and $R^2$ are hydrogen, $R^3$ is 2'-isopropoxy and $R^4$ is hydroxy.

6. The compound according to claim 1, wherein $R^1$ and $R^2$ are hydrogen, $R^3$ is 2'-methyl and $R^4$ is diethylamino.

7. The compound according to claim 1, wherein $R^1$ and $R^2$ are hydrogen, $R^3$ is 4'-isopropoxy and $R^4$ is diethylamino.

8. The compound according to claim 1, wherein $R^1$ and $R^2$ are hydrogen, $R^3$ is 4'-t-butyl and $R^4$ is hydroxy.

9. The compound according to claim 1, wherein $R^1$ and $R^2$ are hydrogen, $R^3$ is 4'-n-pentyl and $R^4$ is hydroxy.

10. A method of treating a human or non-human mammal suffering from an allergic disease, or an inflammation which comprises administering to the sufferer an effective amount of the compound according to claim 1.

11. A pharmaceutical composition for the treatment of allergic diseases, or inflammation, which comprises an effective amount of the compound according to claim 1 together with a pharmaceutically acceptable carrier therefor.

* * * * *